(12) United States Patent
Mirme

(10) Patent No.: US 7,230,431 B2
(45) Date of Patent: Jun. 12, 2007

(54) INTEGRATING ELECTROMETER AMPLIFYING CIRCUIT

(76) Inventor: Aadu Mirme, Salme 42c, 50106 Tartu (EE)

( * ) Notice: Subject to any disclaimer, the term of this patent is extended or adjusted under 35 U.S.C. 154(b) by 0 days.

(21) Appl. No.: 10/765,740

(22) Filed: Jan. 27, 2004

(65) Prior Publication Data
US 2005/0162173 A1    Jul. 28, 2005

(51) Int. Cl.
*G01R 29/12* (2006.01)
(52) U.S. Cl. .............. 324/458; 324/457; 324/123 C; 324/751
(58) Field of Classification Search ............... 324/458, 324/457, 740–751, 123 C; 323/280; 327/67
See application file for complete search history.

(56) References Cited

U.S. PATENT DOCUMENTS

| 4,117,332 | A | | 9/1978 | Felton ................. 250/374 |
| 5,278,490 | A | * | 1/1994 | Smedley ............... 323/284 |
| 5,565,761 | A | * | 10/1996 | Hwang ................ 323/222 |
| 5,617,306 | A | * | 4/1997 | Lai et al. .............. 363/17 |
| 5,742,151 | A | * | 4/1998 | Hwang ................ 323/222 |
| 6,519,167 | B1 | * | 2/2003 | Nguyen ............... 363/41 |
| 6,628,106 | B1 | * | 9/2003 | Batarseh et al. ....... 323/222 |
| 6,781,352 | B2 | * | 8/2004 | Athari et al. .......... 323/222 |
| 6,963,190 | B2 | * | 11/2005 | Asanuma et al. ...... 323/283 |

FOREIGN PATENT DOCUMENTS

| DE | 19824744 | 3/1999 |
| WO | WO90/13829 | 11/1990 |
| WO | WO99/41585 | 8/1999 |

* cited by examiner

*Primary Examiner*—Andrew H. Hirshfeld
*Assistant Examiner*—Marina Kramskaya
(74) *Attorney, Agent, or Firm*—Patterson, Thuente, Skaar & Christensen, P.A.

(57) ABSTRACT

An aerosol particle spectrometer utilizes a high voltage central electrode and a series of annular, axially arranged collector electrodes maintained at ground, for collecting positively charged particles suspended in an aerosol flowing between the electrodes. Each collector electrode provides current to an integrating electrometer including circuitry that rapidly charges and discharges the integrating capacitor during a brief reset cycle, to generate accurate particle characterizing information based on low currents, with high bandwidth and high dynamic range, virtually in real time.

6 Claims, 11 Drawing Sheets

INTEGRATING ELECTROMETER AMPLIFYING CIRCUIT

BACKGROUND OF THE INVENTION

The present invention relates to devices for measuring electrical currents, and more particularly to integrating electrometers for measuring fluctuating currents. The invention further relates to instruments that use integrating electrometers to measure electrical currents to generate particle concentration distributions based on electrical mobility.

Since the late 1960s, those skilled in the art have relied on electrical mobility in a variety of instruments for counting and sizing the particles in aerosols, i.e. suspensions of particles in gaseous media. One such instrument is shown schematically in FIG. 1. An aerosol including a polydisperse particulate suspension is introduced into a cylindrical housing 1 at an entrance 2 where an electrical charge is applied to the particles. A sheath flow of filtered air is introduced to the housing through a conduit 3. A cylindrical center electrode 4 is maintained at a high voltage to attract the charged particles, while an outer wall 5 of the housing is maintained at ground. As the aerosol and sheath flows merge and proceed downward, the charged particles move inwardly toward electrode 4 at different rates that depend on their electrical mobility. Particles with higher mobility, typically the smaller particles, impinge upon electrode 4 above a slot 6. Particles with lower mobilities impinge upon the electrode below the slot. Particles within a desired electrical mobility range enter the slot and travel out through a conduit 7 as a monodisperse aerosol. The remainder of the original aerosol, and sheath flow, exit the instrument through an exhaust conduit 8.

By stepping the voltage applied to electrode 4 through a series of different levels, and separately counting particles exhibiting the desired electrical mobility at each level, this instrument can be used to generate a size distribution or spectrum of the particles. This approach is satisfactory when the particle distribution in the aerosol is expected to remain fairly stable, e.g. in environmental monitoring. However, in situations where the particulate makeup of the aerosol is likely to experience rapid fluctuations, such as in studies of engine exhaust particles, the time required for stepping the electrode voltage through the desired series of levels can interfere with the need to track rapidly changing conditions. Further, this approach cannot be used to generate discreet measurements representing different sizes of particles within the same packet or volume of the aerosol as it progresses through the instrument.

To address these concerns, particle measuring instruments have been developed with modified electrode configurations to enable simultaneous generation of multiple currents for particle sizing. In particular, one recently developed instrument features a single central column electrode biased to one or more positive voltage levels, surrounded by an axially extending series of annular collector electrodes maintained at ground. Smaller, higher-mobility particles are collected at the upstream electrodes, while larger, lower-mobility particles are collected at the downstream electrodes. Each electrode generates its own measurement current, based on the collection of particles within its range of electrical mobility, which is used to represent a particle size range. Accordingly, multiple size measurements are taken simultaneously, with no need to step through multiple levels of biasing voltage. Further, individual volumes or packets of the aerosol can be measured in multiple channels or stages, each corresponding to one of the collector electrodes, as the aerosol volume proceeds through the instrument.

Electrical currents generated by particle collection at the annular electrodes are measured by electrometer amplifiers, each generating an output voltage representative of the incoming current. Traditionally, the electrometer amplifier circuits have employed operational amplifiers with low input bias currents and high value resistors in their feedback loops. Currents to be measured are provided to the negative input terminals of the operational amplifiers. As a result, the output voltage U is generated according to the formula $U=-IR$, where I is the incoming current and R is the resistance.

While this arrangement is better suited to track changing particulate levels in monitored aerosols, thermal noise due to the high value feedback resistor requires use of a low pass filter to remove the noise component. This limits the bandwidth of the measuring circuit, reducing its ability to accurately follow fluctuations in particle sizes and concentrations. Accordingly, this approach is not entirely satisfactory for following the transients inherent in engine exhausts.

Accordingly, it is an object of the present invention to provide an instrument for characterizing aerosol particles based on their electrical mobility, with the capacity to accurately classify particles by size, based on low amplitude particle collection currents subject to rapid fluctuations.

Another object is to provide an aerosol particle spectrometer capable of generating, simultaneously, multiple currents representative of particles in different ranges of electrical mobility, sampled at a high rate to achieve improved tracking of fluctuations in the multiple currents.

A further object is to provide an integrating electrometer circuit configured to generate an output that rapidly and accurately characterizes the incoming current, to provide more reliable tracking of rapidly fluctuating incoming currents.

Yet another object is to provide a process for measuring an electrical current by integrating the current over a range predetermined by at least one threshold signal level, using the threshold level to rapidly reset an output based on the incoming current by positively driving the output back into the operating range for further integration.

SUMMARY OF THE INVENTION

To achieve these and other objects, there is provided an integrating electrometer and rapid reset circuit. The circuit includes an operational amplifier with an integrator input for receiving an incoming electrical current, an integrator output for generating integrator output voltage changes in a predetermined first direction and at a rate determined by a level of the incoming current, and a feedback loop including an integrating capacitor. A first circuit is provided for detecting a voltage along the feedback loop to provide a condition-monitoring voltage that undergoes changes in response to the incoming current consistent with the changes to the integrator output voltage. A voltage source sets a substantially stable first threshold voltage, which determines a first end of an operating range over which the incoming current is integrated. A second circuit is provided for receiving the condition-monitoring voltage and the first threshold voltage. The second circuit detects movement of the condition-monitoring voltage in the first direction beyond the first threshold voltage and out of the operating range. In response to detecting this movement, the second circuit applies a first reset signal to the feedback loop to drive the condition-monitoring voltage in a second and opposite direction to a point within the operating range for further integration of the incoming current.

Preferably, the circuit further includes a voltage source for setting a substantially stable second threshold voltage which determines a second, opposite end of the operating range. A third circuit receives the condition-monitoring voltage and the second threshold voltage, and detects movement of the condition-monitoring voltage in the second direction beyond the second threshold voltage out of the operating range. In response to detecting such movement in the second direction, the second circuit applies a second reset signal to the feedback loop, to drive the condition-monitoring voltage in the first direction, to a point back within the operating range for further integration of the incoming current.

In a particularly preferred approach, the condition-monitoring voltage when in the operating range is higher than the first threshold voltage, lower than the second threshold voltage, and is reduced during integration of the incoming current. Then, the second circuit is configured to provide a stable low voltage to the feedback loop during integration. Upon sensing that the condition-monitoring voltage has been reduced to a level below the first threshold voltage, the circuit switches to apply a stable high voltage to the feedback loop to rapidly charge the integrating capacitor, thus driving the condition-monitoring voltage upward.

Further in this approach, the third circuit generates a stable high voltage during normal integration. Upon sensing that the condition-monitoring voltage has increased to a level above the second threshold voltage, typically as a result of the rapid charging of the integrating capacitor, the third circuit provides the second reset signal by switching from the high voltage to a stable low voltage, which rapidly discharges the capacitor.

A further preferred feature is a power control circuit coupled to receive the first reset signal from the second circuit, and coupled to provide power to the operational amplifier. During integration, the power control circuit provides a stable, high level voltage to the op amp. In response to receiving the first reset signal from the second circuit, the power control circuit switches its output from the high voltage level to a steady low voltage level, thus shutting off power to the amplifier. When the second circuit terminates the first reset signal, the power control circuit responds by restoring power to the op amp.

Yet another advantageous feature is a charge limiting circuit coupled between the second circuit and the feedback loop, to prevent excess charging of the integrating capacitor.

One favorable aspect of the present invention is that the amplifier or circuit gain is determined by the integrating capacitor, rather than by a high value feedback resistor. This removes a major source of circuit noise, essentially limiting circuit noise to that of the operational amplifier itself. With no need to limit the bandwidth of the integrating circuit output, the output is provided over a broader bandwidth for improved tracking of fluctuations in the aerosol particle suspension.

The integrating electrometer circuitry is somewhat more complex than the traditional differential amplifier circuitry, in that the integrating capacitor needs to be repeatedly charged or discharged, depending on whether current integration decreases or increases the integrating circuit output. Also, resetting the capacitor represents "down time" when the output of the integrating circuit does not reliably represent the incoming current, giving rise to the need to selectively ignore data generated during a reset stage.

In accordance with the present invention, these concerns are addressed first by limiting reset cycle time. To this end, the upper and lower threshold voltages are used to trigger charging and discharging of the integrating capacitor, respectively. Depending upon which threshold the condition-monitoring voltage passes when leaving the predetermined operating range, the reset circuitry applies either a high voltage to rapidly charge the capacitor, or a low (essentially zero) voltage to rapidly discharge the capacitor.

When integration reduces the integrating circuit output as in the preferred version discussed above, each capacitor reset cycle preferably includes a rapid charge, followed immediately by a rapid discharge. The discharge, terminated by entry of a descending condition-monitoring voltage into the operating range, positions that voltage near the upper limit of the range for another integrating cycle in which the condition-monitoring voltage is gradually reduced.

As a result of the positive or "hard" charging and discharging of the integrating capacitor, the reset cycle is extremely short in comparison to the typical measurement (integration) cycle. For example, in one version of the circuit, each integration cycle takes at least one second, while the reset cycle takes about one millisecond. Accordingly, even when the integrating circuit output is sampled frequently, e.g. ten times per second, the probability of sampling data generated during reset cycles is minimal.

Nonetheless, to ensure that such data are ignored, the integrating circuit advantageously incorporates logic for comparing each sample with its immediately preceding sample and immediately following sample, and computing the differences between samples. The differences are compared to a threshold selected to allow for differences that reflect substantial fluctuations in the aerosol makeup, yet exclude the much larger differences that occur due to rapid charging or discharging of the integrating capacitor. Thus, any data point that exceeds the difference threshold when compared to adjacent data points, is replaced by an interpolated result between the adjacent valid data points.

Thus, integrating electrometer circuits according to the present invention more accurately measure current fluctuations over a wide dynamic range.

Another aspect of the present invention is an instrument for characterizing aerosols subject to fluctuations in particle concentration. The instrument has a conduit for guiding an aerosol in a substantially non-turbulent flow at a substantially constant volumetric flow rate toward and along a particle measuring region. The aerosol consists essentially of a suspension of particles in a gaseous medium. A first electrode configuration is disposed along the measuring region. A second electrode configuration, including at least one collector electrode, is electrically isolated from the first electrode configuration and spaced apart from the first electrode configuration to allow the aerosol to flow between the first and second electrode configurations as it moves through the measuring region. A voltage source selectively biases the first electrode configuration relative to the second electrode configuration to generate an electrical field along the measuring region. Particles of the aerosol that carry a charge of a selected polarity, when carried through the measuring region, are attracted toward the second electrode configuration to cause a portion of the charge-carrying particles to collect at the collector electrode. A current measuring device is coupled to the collector electrode for receiving an incoming electrical current from the collector electrode generated by the collecting of the charge-carrying particles. The current measuring device includes an integrating component for integrating the incoming electrical current to produce an output voltage corresponding to the current. The current measuring device also includes a reset component for selecting a range of output voltages over which the current is integrated, and for resetting the integrating component in response to movement of the output voltage outside of the selected range, to reposition the output voltage within the operating range or further integration of the incoming current.

In a preferred version of the instrument, the second electrode configuration includes an axially extending series of annular collector electrodes, concentric on an elongate axially extending electrode that provides the first electrode configuration. Particles with higher electrical mobilities collect along the upstream electrodes, while particles with lower mobilities collect along the downstream electrodes. Each collector electrode provides current to its own associated current measuring device, resulting in multiple sets of current characterizing data to provide a size distribution of the aerosol particles. Preferably, readings from the upstream collectors are selectively delayed, to synchronize the measuring device outputs corresponding to a volume or packet of the aerosol as that volume travels through the measuring region.

Accordingly, aerosol particle measuring instruments constructed according to the present invention not only can produce finely divided aerosol particle size distributions, but also can accurately follow fluctuations in particle concentrations, both at large and within the size range or channel associated with each collector electrode, for a more comprehensive examination of engine exhaust aerosols and other rapidly fluctuating aerosols.

IN THE DRAWINGS

For a further understanding of the above and other features and advantages, reference is made to the following detailed description and to the drawings, in which:

FIG. 1 schematically illustrates a prior art instrument for distinguishing aerosol particles based on their electrical mobility;

FIG. 2 schematically illustrates an aerosol particle spectrometer constructed in accordance with the present invention;

Figure 4:
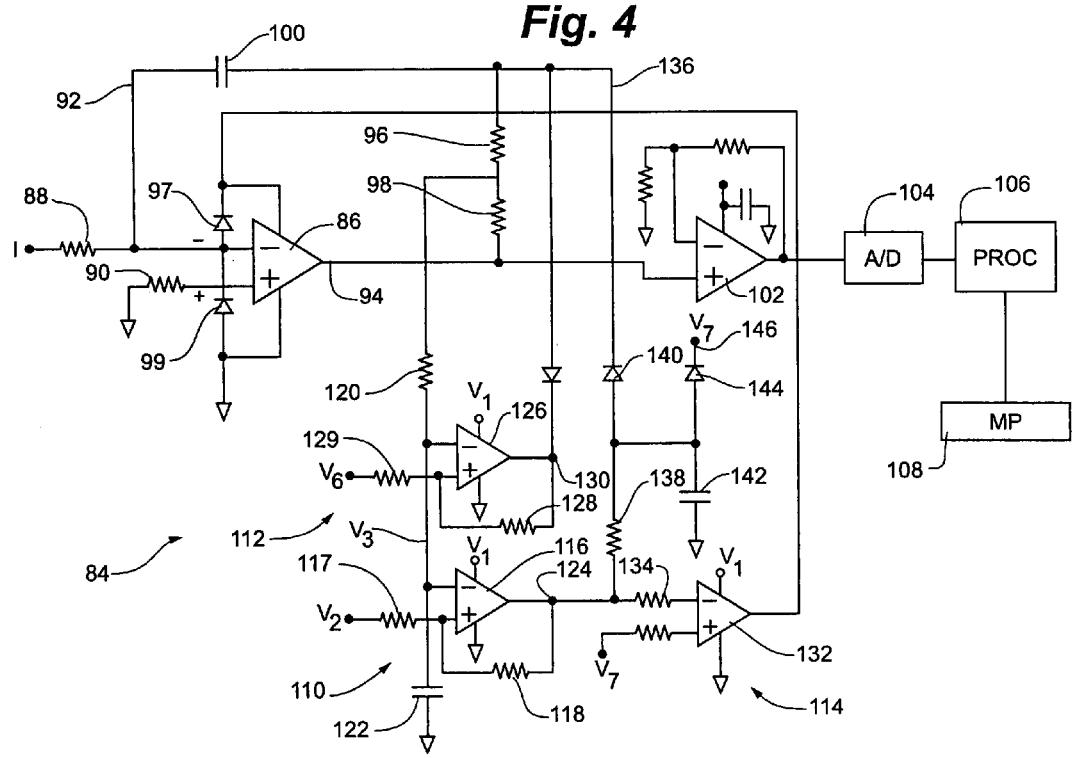
FIG. 4 is a schematic representation of a current measuring circuit used in the spectrometer of FIG. 2.
Figure 5:
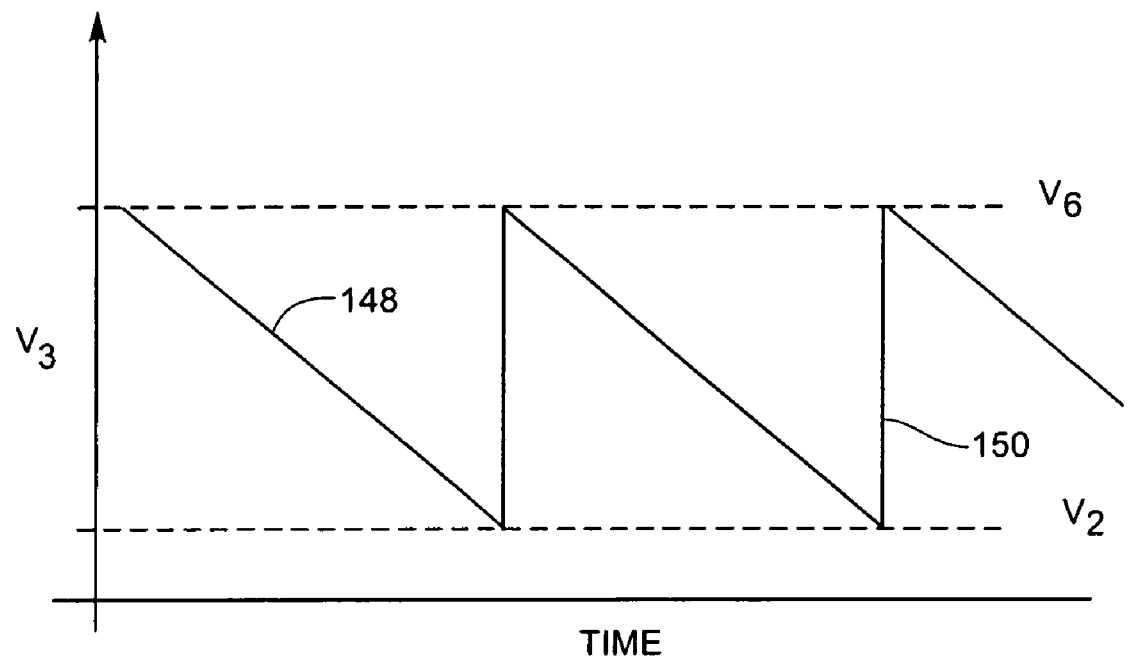
Figure 6:
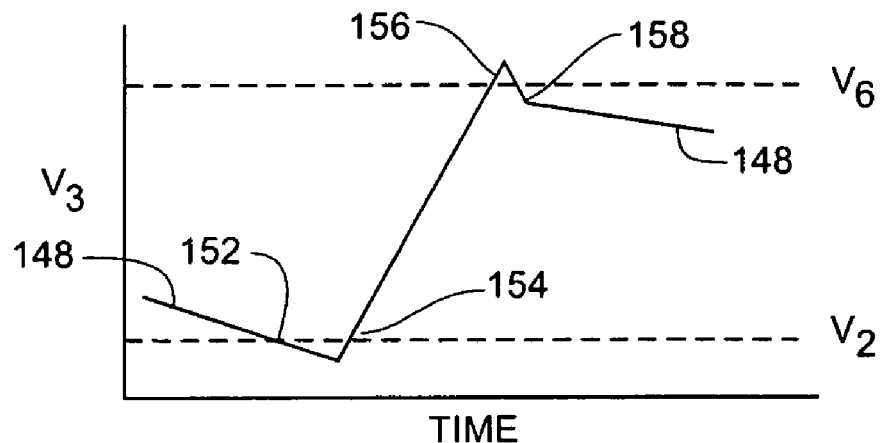
Figure 7:
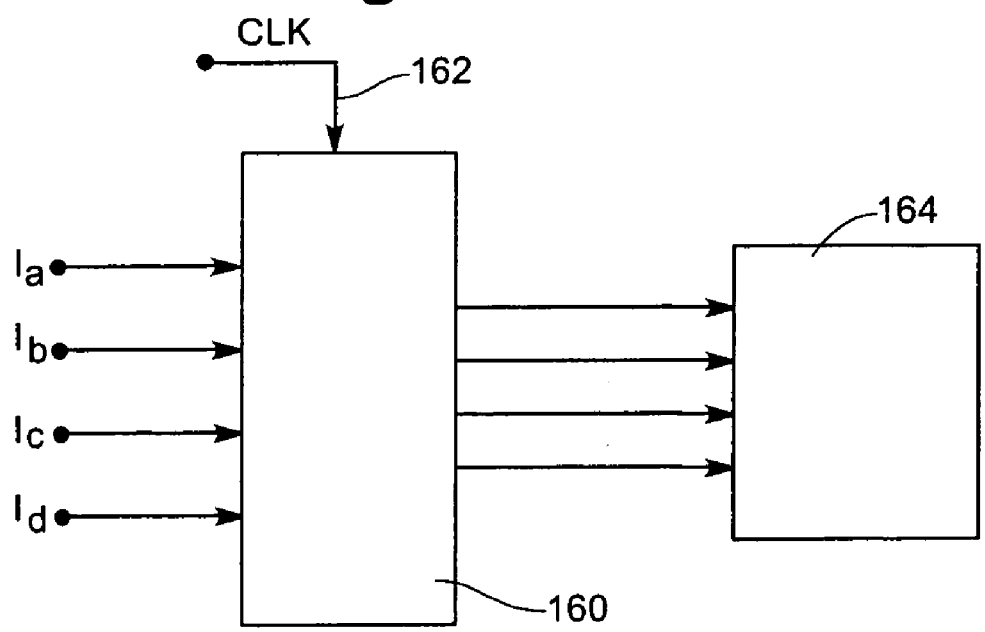
Figure 8:
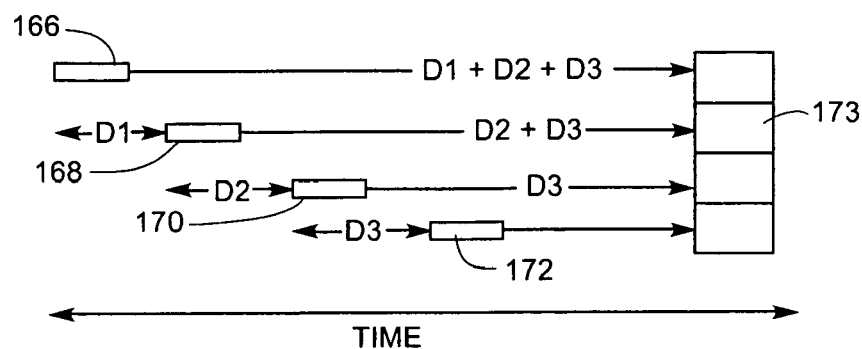
Figure 9:
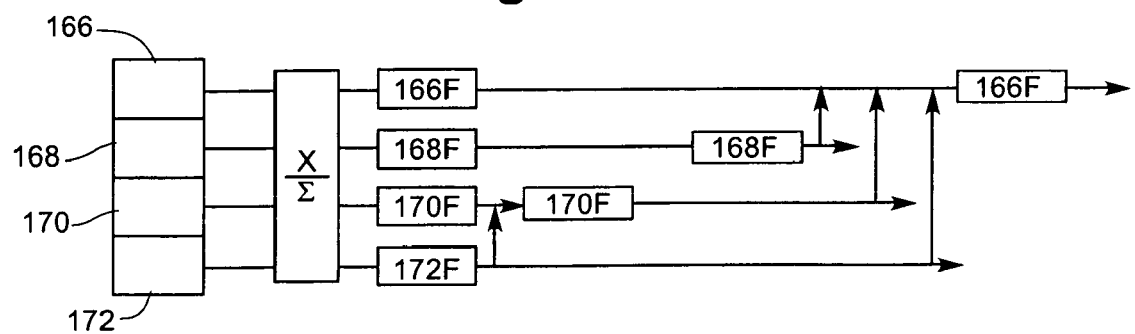
Figure 10:
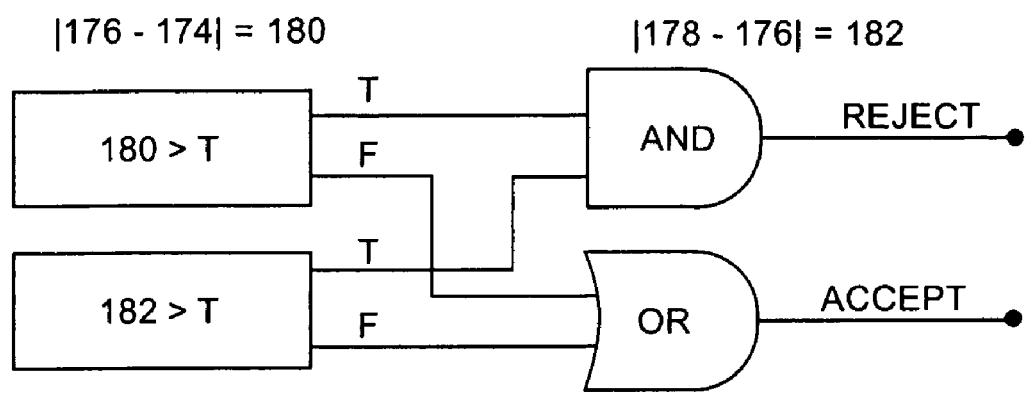

FIG. 5 graphically illustrates voltage changes over several operating cycles of the circuit in FIG. 4;

FIG. 6 graphically illustrates a reset segment of one of the operating cycles;

FIG. 7 illustrates a preferred construction associating several circuit outputs with a single A/D converter;

FIGS. 8 and 9 diagrammatically illustrate synchronization and error correction logic for handling multiple integrator circuit outputs;

FIG. 10 schematically illustrates logic for avoiding use of data associated with reset cycles;

FIGS. 11–14 illustrate alternative current integrating circuits; and

Figure 15:
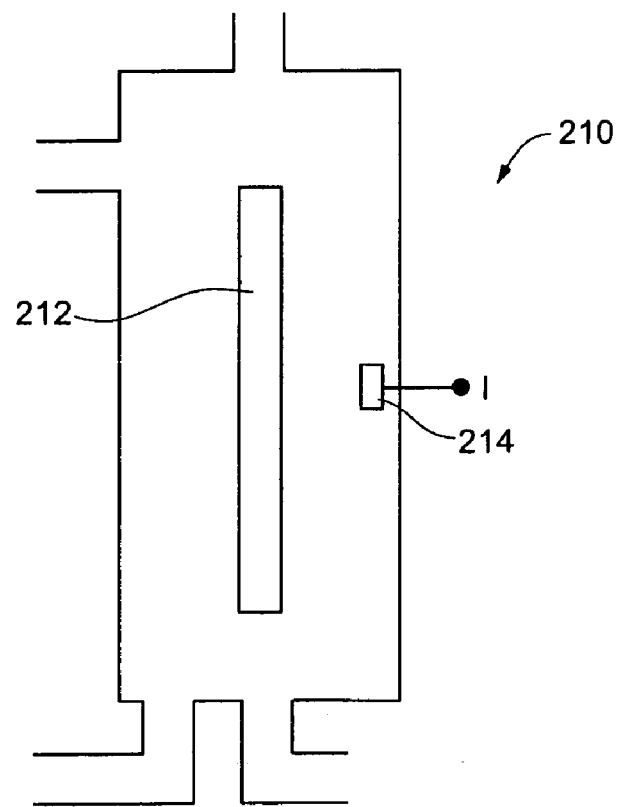

FIG. 15 illustrates an alternative aerosol particle characterizing instrument constructed in accordance with the present invention.

DETAILED DESCRIPTION OF THE PREFERRED EMBODIMENTS

Figure 1:
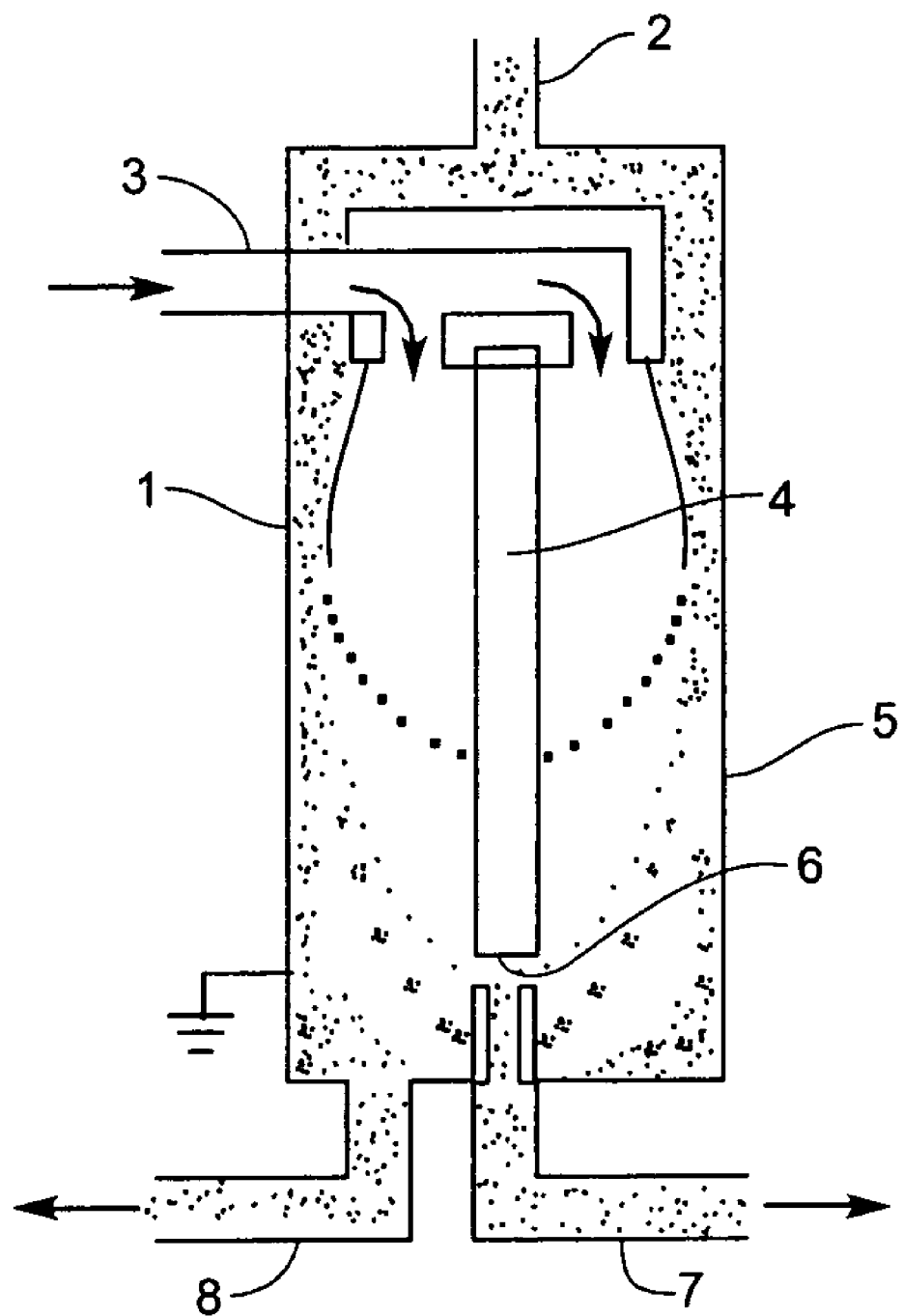
Figure 2:
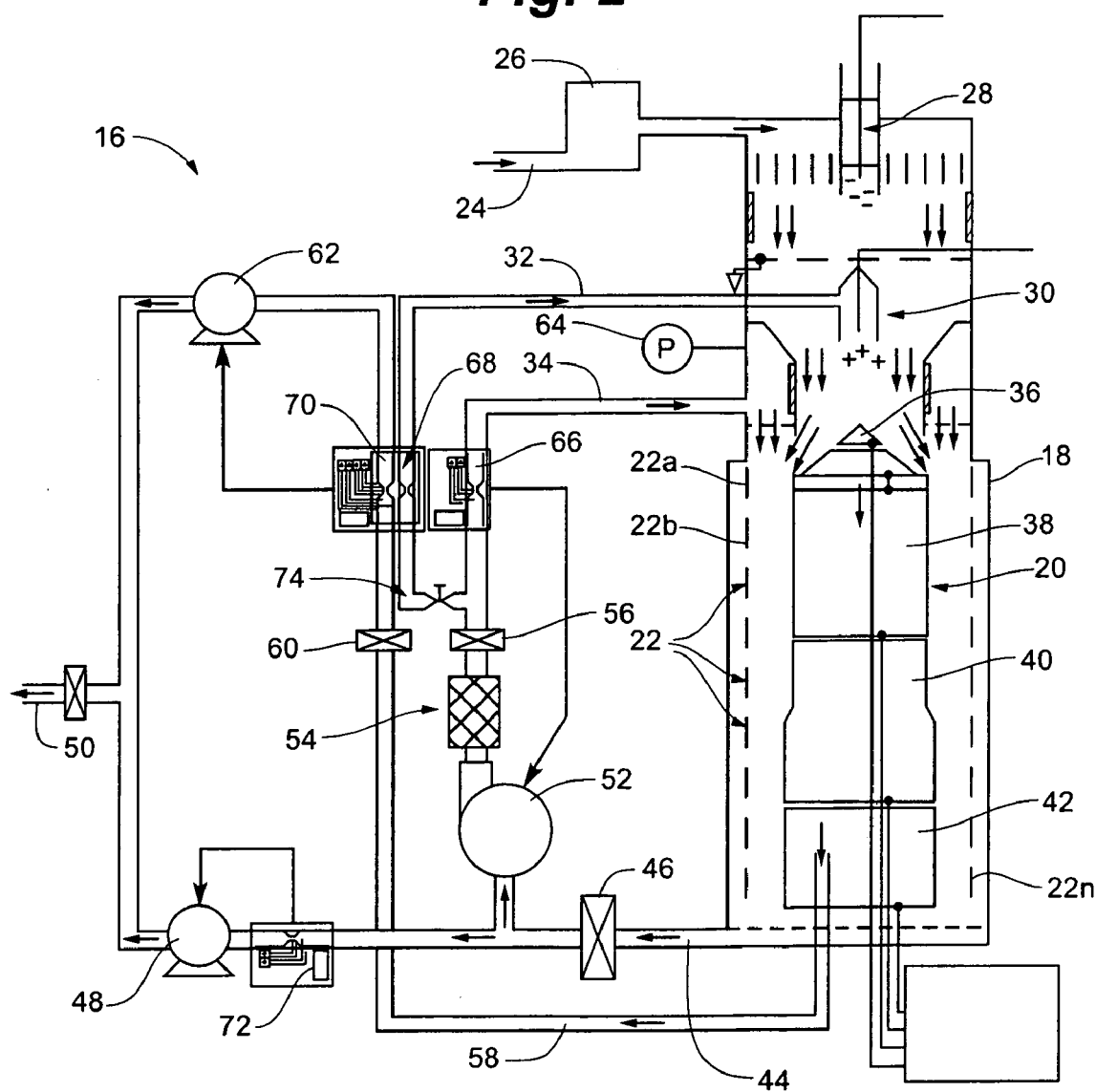

Turning now to the drawings, there is shown in FIG. 2 the structural components of an aerosol particle spectrometer 16 constructed in accordance with the present invention. Primary structural components include a housing 18 and two electrode assemblies or configurations inside the housing: a center electrode assembly 20, and an assembly of multiple annular collector electrodes 22a through 22n arranged in an axially extending series, spaced apart from each other and electrically isolated from each other. Collector electrodes 22 are concentric with and surround the center electrode assembly.

Conduits associated with housing 18 guide a combination of aerosol and other gaseous flows into and out of the housing. An aerosol entry conduit 24 receives an incoming aerosol at a rate of about 10 liters per minute, at approximately atmospheric pressure. A cyclone 26 near the entry conduit removes larger particles from the aerosol, for example, particles with diameters exceeding 1 micron. Downstream of the cyclone, a corona discharge element 28 is biased to generate negative ions, which mingle with the incoming aerosol to apply negative charges to the suspended particles. Element 28 functions as a preliminary charger, intended to reduce the number of highly positively charged particles, and to prevent over charging in a primary charger downstream.

The primary charger is a corona discharge element 30 biased to generate positive ions that intermix with the aerosol to apply positive charges to the particles. Due to the preliminary charge, the primary charge applies a more predictable net positive charge on the particles. A conduit 32 provides a charge facilitating flow of filtered air, at a rate of about 0.6 liters per minute (lpm). This flow tends to carry positive charges away from the tip of discharge element 30 and toward the aerosol, to facilitate a more rapid, more even charging of the particles.

Downstream of the primary charger, a 2 lpm central portion of the flow is removed, due to the tendency toward less uniform charging in the central region. The remainder of the flow is merged with a sheath air flow provided through a conduit 34 at a rate of about 39.4 lpm to provide a combination of aerosol and sheath air flowing through the housing at 48 lpm.

The center electrode assembly and the collector electrode assembly are selectively charged relative to each other to create an electrical field that acts upon the charged particles. In particular, electrode assembly 20 includes several electrode sections biased to increasingly higher positive voltages in the direction of particle travel. An initial electrode section 36 is maintained at an extremely low voltage, essentially zero. Downstream electrode sections 38, 40 and 42 are biased to 85 volts, 470 volts, and 1,200 volts, respectively. Meanwhile, collector electrodes 22 are maintained at ground. Thus, the electrical field is strengthened considerably in the downstream direction. This strengthening of the field considerably shortens the length of the center electrode assembly and corresponding extension of collector electrodes, as compared to an instrument without such field strengthening, to measure a range of particle sizes (electrical mobilities) over a desired range, in this case over two orders of magnitude.

Electrode section 40 illustrates another technique for shortening the required electrode length: enlarging the center electrode diameter in the downstream direction, to shorten the distance for particle travel from a medial location between electrode assemblies, to one of the collector electrodes.

As the charged particles are carried axially along the measuring region, i.e. between the electrode assemblies, the positively charged center electrode sections repel the particles outwardly toward the grounded collector electrodes.

To the extent practicable, the primary and secondary chargers are configured to apply a single charge to each particle. Assuming the particles are identically charged, the smaller particles subject to less drag force are more easily diverted from the axial path and propelled toward the collector electrode assembly. Consequently, the smaller particles tend to collect along the upstream collector electrodes, and the larger particles tend to collect along the downstream collector electrodes.

While not illustrated in FIG. 2, each collector electrode 22 generates an electrical current in proportion to the charge on the particles it collects. As a result, the current provides an indication of the number of particles collected. More particularly, the currents of all collector electrodes 22 cooperate to indicate for each collector electrode a degree of particle collection relative to the other collector electrodes, and a fractional share of the particles collected across the entire spectrum.

Downstream of the electrode assemblies, a conduit 44 provides an exit for the 48 lpm aerosol/sheath air flow. After filtration at 46, a portion of the flow (8 lpm) is drawn by an exhaust pump 48 toward an exhaust exit 50. The remaining 40 lpm is directed by a sheath air blower 52 through a heat exchanger 54 and filter 56, back to conduit 34 to replenish the sheath air.

A conduit 58 provides an exit for the extracted central 2 lpm flow mentioned above, filters the flow at 60 and provides the flow to the exhaust exit through an extraction pump 62. The various flows are sensed and controlled by a pressure sensor 64, flow monitors 66, 68, 70 and 72, blower 52, pumps 48 and 62, and a valve 74 between conduits 32 and 34.

Figure 3:
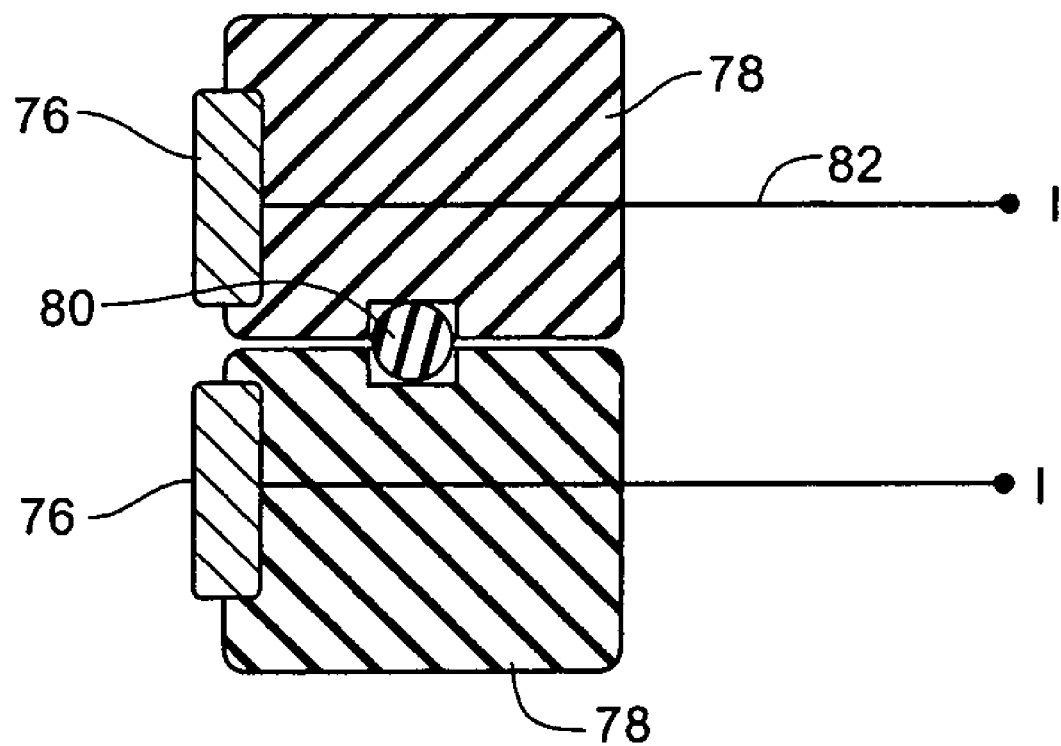
FIG. 3 is an enlarged partial view of the spectrometer in FIG. 2.

FIG. 3 is a sectional view showing collector electrodes 22a and 22b in more detail. The operative portion of each electrode is a metal ring 76. The ring is formed into a ring-shaped casing 78, formed of an electrically insulative material selected for low piezoelectric properties in addition to its high electrical resistance. This structure provides a large surface area for high surface electrical resistance between adjacent metal rings 76, while attaining a relatively narrow spacing between the rings. Finally, o-ring seals 80 are mounted between adjacent rings 76 to provide a leak-tight column. Each electrode 22 further includes a conductor 82 coupled to ring 76 for conducting an electrical current away from the ring as it collects charged particles.

Each of the collector electrodes, in conjunction with its collection of charged particles, produces an electrical current, and provides the current to an electrical current measuring device individually associated with the electrode. In spectrometer 16 (FIG. 2), each of the measuring devices is provided in the form of an integrating electrometer circuit 84, as shown in FIG. 4. Circuit 84 includes an integrating component, and an integrator resetting component to confine integration of the incoming current to an operating range of output voltages, precisely set by upper and lower voltage thresholds. The integrating component includes an operational amplifier 86 with a negative input terminal that receives the collector electrical current through a resistor 88. The positive input terminal is maintained at ground along a path that incorporates a resistor 90. The operational amplifier gain is determined by a feedback loop 92 beginning at an amplifier output terminal 94 and including a resistor 96, a resistor 98 and an integrating capacitor 100. Diodes 97 and 99 have low leakage current and matched thermal properties, and protect the op amp against damage from input voltages (to power input terminals) greater than the op amp supply voltage. These diodes also assist in rapid charging and discharging of integrator capacitor 100, as is later explained. The output of amplifier 86 is provided to a buffer amplifier 102 having unity gain. In a particularly preferred version of the integrating electrometer circuit, the foregoing components are formed on a single integrated circuit (IC) chip, a result that can be achieved with conventional silicon chip fabrication techniques.

The output of amplifier 102, i.e. the analog integrator output, is provided to an analog/digital converter 104. The digital signal from A/D converter 104 is provided to a digital processor 106, preferably an integrated circuit chip. Chip 106 is connected to a microprocessor 108, which receives data from the chip, and also stores and loads software programs into processor 106 for use by the processor in handling digital data from A/D converter 104. Microprocessor 108 is similarly coupled to the digital processors associated with the other collector electrodes, and accordingly is configured to handle data representing the entire spectrum.

The reset component of circuit 84 includes a comparator 110 that governs charging of the integrating capacitor, a comparator 112 that controls discharging of capacitor 100, and a power control component 114.

Comparator 110 includes a comparator amplifier 116 biased to a positive voltage $V_1$ and having a feedback loop that includes a resistor 118. The positive terminal of amplifier 116 is biased to a constant low level threshold voltage $V_2$ that determines the lower end of an operating range over which the integrating component integrates incoming current.

The negative input terminal of comparator amplifier 116 is coupled to feedback loop 92 between resistors 96 and 98, to receive a comparator input voltage. The comparator input voltage varies in response to the incoming current in a manner consistent with the variance of the integrator output. More particularly, the integrator output and the voltage applied to the negative input of amplifier 116 respond to incoming current by changing in a selected first direction (i.e., both are reduced). Further, these voltages are changed at a rate that increases in proportion to the level of the incoming current. For convenience, the voltage input to amplifier 116 can be thought of as a condition-monitoring voltage $V_3$, because it reflects a condition of the integrating component of circuit 84, namely a voltage along feedback loop 92. One difference between these signals is that changes in the condition-monitoring voltage lag changes in the integrator output, by a time delay determined by the time constant of an RC network provided by a resistor 120 and capacitor 122 between amplifier 116 and feedback loop 92.

The output of comparator amplifier 116 at an output terminal 124 is switched between two steady voltage levels: a high voltage level $V_4$ if condition monitoring voltage $V_3$ is lower than threshold voltage $V_2$, and a low voltage level $V_5$ if input voltage $V_3$ is higher than threshold voltage $V_2$. Resistors 117 and 118 cooperate to provide hysteresis, for stable transitions between the high and low voltage levels.

Comparator 112 includes an amplifier 126 that receives power at voltage level $V_1$, and has a resistor 128 along its feedback loop. The negative input terminal of amplifier 126 receives the condition monitoring voltage, while the positive input terminal is biased to a constant upper threshold voltage $V_6$ that determines an upper end of the operating range. Comparator amplifier 126 is configured to generate, alternatively, two outputs at its output terminal 130: the high voltage level $V_4$ when the condition monitoring voltage is less than threshold voltage $V_6$, and the low voltage level $V_5$ when the condition monitoring voltage is above threshold voltage $V_6$. Resistors 128 and 129 function in the same manner as resistors 117 and 118, to stabilize transitions in the output of amplifier 126 between the high and low voltage levels.

Power control component 114 includes an amplifier 132 powered at voltage $V_1$, and coupled to output terminal 124 to receive the output voltage of amplifier 116 through a resistor 134 to its negative input terminal. The positive input terminal of amplifier 132 is biased to a constant intermediate positive voltage level $V_7$, less than high voltage level $V_4$ and higher than low voltage level $V_5$. Amplifier 132 is configured to generate two alternative outputs, as governed by the input from amplifier 116: high voltage level $V_4$ when receiving the low voltage level $V_5$ from amplifier 116, and low voltage level $V_5$ when receiving the high voltage level $V_4$ from amplifier 116. Amplifier 132 provides the power input to op amp 86. The high voltage level from amplifier 132 powers amplifier 86, while the low level voltage from amplifier 132 shuts off power to amplifier 86.

Output terminal 124 of comparator amplifier 116 is coupled to feedback loop 92 to provide a conductive path 136 for charging integrating capacitor 100. Components along the conductive path include a resistor 138, and a diode 140 with its positive direction aligned with charging current flow. Also coupled to the path are a limiting capacitor 142 and a diode 144, with a terminal 146 ahead of diode 144 biased to intermediate voltage level $V_7$.

The operation of the electrometer circuit 84 can be considered in conjunction with FIGS. 5 and 6, which depict how condition-monitoring voltage $V_3$ changes over time. FIG. 5 illustrates several cycles, each including a normal current integration segment 148 and a capacitor reset segment 150, during which voltage $V_3$ is repositioned for initiation of another integrating segment. Integrating segment 148 is shown with a gradual slope as compared to a much steeper, nearly vertical slope for reset segment 150, to indicate that the integrating segment occupies most of the cycle time. In fact, the integrating segment typically takes at least one second. The time for this segment can vary considerably, because the rate at which the condition-monitoring voltage is reduced, i.e. the slope (or slopes) of each segment 148, depends on the level (or levels) of the incoming current.

In contrast, each reset segment 150 requires only about one millisecond. The time for the reset cycles is substantially uniform, because each reset segment involves the same reset steps.

Although FIG. 5 shows each capacitor integrating segment 148 with the same negative slope to simplify the illustration, it should be understood that in actual practice the slope during integration depends on the amplitude of the incoming current. Thus, the slope during any integrating segment can vary from zero (horizontal) in the absence of incoming current, to a steepest slope corresponding to a maximum expected current level. All none-zero slopes are negative, reflecting the fact that the condition-monitoring voltage moves in the same direction in response to the incoming current.

The cycle of operation of circuit 84 is conveniently considered to begin with normal integration of the incoming current, which begins with condition-monitoring voltage $V_3$ just below the upper threshold voltage level $V_6$. With positive current I provided to the negative terminal of op amp 86, integration moves the integrator output gradually downward, which also reduces condition-monitoring voltage $V_3$, subject to the previously mentioned time delay.

When the condition-monitoring voltage is reduced below lower threshold voltage level $V_2$ (FIG. 4), the output of comparator amplifier 116 is switched from the low voltage level to the high voltage level. With reference to FIG. 6, which illustrates one of the reset segments, the reset segment starts at 152 when condition-monitoring voltage $V_3$ falls below low threshold voltage $V_2$, which switches the output of amplifier 116 from the low voltage level $V_5$ to the high level voltage $V_4$. The high voltage level at output terminal 124 initiates a rapid charging of integrating capacitor 100, and also limiting capacitor 142, through resistor 138. Capacitor 100 is charged rapidly, limited only by the time constant of resistor 138 and the combination of capacitor 100 and capacitor 142.

Virtually simultaneously with the initiating of charging, amplifier 132 switches from the high voltage to the low voltage output in response to receiving the high voltage from amplifier 116, to shut off power to operational amplifier 86. Despite the absence of power, the integrator output voltage rises rapidly.

Capacitor 142 and diode 144 prevent excessive charging of integrating capacitor 100, primarily to protect the input to A/D converter 104. Capacitor 142 contributes to the time constant, so that capacitor 100 is charged at a lower rate than if it were being charged alone. Also, should voltage between capacitor 142 and diode 144 rise above intermediate voltage $V_7$ during charging, current will drain through diode 144 to limit the maximum voltage applied to capacitor 100 and to protect A/D converter 104.

Condition-monitoring voltage $V_3$ also rises during capacitor charging, subject to the previously discussed time delay. When voltage $V_3$ increases to the lower threshold voltage level as indicated at 154 in FIG. 6, the voltage at output terminal 124 is switched back to the low level, which terminates the charging of capacitor 100, and acts through amplifier 132 to reapply power to op amp 86.

The condition-monitoring voltage continues to rise until it exceeds the upper threshold voltage $V_6$ as indicated at 156, switching the output of comparator amplifier 126 from the high voltage level to the low voltage level $V_5$. The low voltage is applied to feedback loop 92, which initiates a rapid discharge of the integrating capacitor. This reduces the integrator output, and reduces the condition-monitoring voltage, subject to the RC delay.

When voltage $V_3$ drops below the upper threshold voltage level $V_6$ (at 158), amplifier 126 switches its output back to the high voltage level. The high voltage level terminates a discharge, thus to initiate the next normal integration cycle with voltage $V_3$ just below upper threshold voltage level $V_6$.

A salient feature of the present invention is the use of on-chip protection diodes 97 and 99 to provide a current path to assist in charging and discharging capacitor 100. Specifically, diode 97 provides a current path between capacitor 100 and amplifier 86, during charging of capacitor 100 and when power to amplifier 86 is shut off because amplifier 132 has switched to its low voltage level output. Current flows through diode 97, bypassing the high-impedance power input to amplifier 86. If necessary or desired, diode 99 can be used to provide a similar current path to bypass the power input when discharging capacitor 100.

Electrometer circuit 84 is capable of rapidly generating measurements of extremely low incoming currents, e.g. in the femto-amp range. The circuit allows amplification and digitization of the incoming current at a rapid rate (ten samples per second or higher), with an A/D converter resolution of greater than 20 bit RMS, equivalent to a dynamic range of $10^6$, with extremely low background noise.

As compared to the previously used electrometer circuits based on feedback resistors, integrating electrometer circuit 84 is more complex, involves the need to repeatedly reset the integrating capacitor, and requires differentiation of the electrometer circuit output. These factors, however, are outweighed considerably by the advantages noted above.

In one highly preferred version of circuit 84, power inputs to the circuit ($V_1$) are maintained at 7.5 v. The intermediate voltage $V_7$ is 5 v, and the upper and lower threshold voltages are 4.7 v and 0.3 v, respectively. The high voltage amplifier outputs are 7.4 v, and the low voltage amplifier outputs are 0 v. Resistors 118 and 128 have resistances of 3 million ohms; resistors 88 and 120, 1 million ohms; resistors 117, 129 and 134, 100,000 ohms; resistor 90, 10,000 ohms; resistor 98, 5,110 ohms; and resistors 96 and 138, 2,740 ohms. Integrator capacitor 100 has a capacitance of 100 pf, with the exception of the first several upstream channels in which the electrometer circuit integrating capacitors have a capacitance of 33 pf. Capacitors 122 and 142 each have a capacitance of 0.1 µf. Apart from the difference in capacitance just noted, the electrometer circuits are substantially identical. Further, it is advantageous to form integrating capacitor 100 with a material having high resistance to dielectric absorption.

FIG. 7 illustrates an alternative, preferred approach in which a single A/D converter 160 receives the integrator outputs from four electrometer circuits associated with consecutive channels or collector electrodes 22. A clocking input 162 drives the A/D converter to obtain a sampling frequency of 40 samples per second, enabling the A/D converter to sample each of the integrator outputs at a frequency of 10 samples per second. The A/D converter provides corresponding digital output to a digital processor 164 preferably in the form of an integrated circuit chip.

The integrator outputs of the different channels, and their corresponding A/D converter outputs, represent raw values that require differentiation. In connection with electrometer circuit 84, processor 106 differentiates the integrator output digitally, by computing the differences between successive samples (digital representations) of the electrometer circuit output. The computed values are proportional to the incoming current.

In addition, the A/D converter outputs are subject to errors inherent in instruments such as spectrometer 16. Accordingly, digital processor 106, or alternatively processor 164, incorporates digital logic to compensate for system errors and to selectively synchronize the channels.

Synchronization is illustrated in FIG. 8, which represents four spectrometer channels, 166, 168, 170 and 172 corresponding to a series of electrodes located progressively downstream. Horizontal spacing between channels represents the time required for a particular volume or packet of the aerosol to travel from one electrode to the next. Specifically, D1 is the time required for the aerosol to travel from the upstream electrode of channel 166 to the next, second electrode. Delay D2 represents the time of travel from the second to the third electrode, and D3 represents travel time from the third electrode to the final, downstream electrode. As indicated, the travel time between an upstream electrode and each downstream electrode is interposed in the channel relating to that electrode, resulting in a synchronized field 173 incorporating the values in all channels associated with the same volume or packet of the aerosol. In one highly preferred version of the device, the actual number of channels is 22, and the travel time from the upstream electrode to the final, downstream electrode is about two seconds.

FIG. 9 schematically represents a correction for an "image charge" effect. Particles that flow past a given collector electrode, although collected on another electrode downstream, influence the charge at the upstream electrode to create an effect known as an image charge. As seen in FIG. 9, digitized integrator outputs from successive channels 166, 168, 170 and 172 are sampled, with a most downstream channel 172 divided by the cumulative channel values to yield a charging fraction for the final channel. Based on a factor determined by a mathematical model, the final channel charging fraction 172F is applied to correct (i.e. to reduce) the charging fraction 170F of the preceding channel. The corrected fraction 170F, and the most downstream fraction 172F, then are applied to correct the next upstream fraction 168F, with similar corrections applied until the initial, upstream fraction is corrected.

While not illustrated, the integrator outputs also are corrected for the presence of multiply charged particles. As indicated above, the preliminary and primary chargers are configured to apply a single positive charge to each particle, to the extent practicable. This notwithstanding, larger particles emerge from the primary charger carrying two or more charges. The multiply charged particles, being more strongly influenced by the electrical field, are collected at electrodes upstream of the electrodes properly associated with their sizes, thus creating a mistaken indication of higher concentrations of smaller particles. This error is compensated by corrective factors based on instrument calibration and mathematical modeling.

Finally, processors 106 (or 164) differentiate the error-compensated data from all channels, to provide data streams that rise and fall in correspondence with increases and decreases in the measured currents.

FIG. 10 illustrates logic for selectively ignoring data generated during reset segments of the operating cycles. Successive sample values 174, 176 and 178 (i.e. digital values representing integrator outputs) are illustrated, with the value 176 being of primary interest. Sample value 176 is compared with previous value 174 to yield a first difference 180, and compared with its next subsequent sample value 178 to yield a second difference 182. Both differences are compared to a threshold T, high enough to accommodate expected fluctuations in aerosol particle concentrations, and considerably lower than the difference between successive sample values of the output voltage, or alternatively of condition-monitoring voltage $V_3$, during the rapid charging or discharging of the integrating capacitor. If only one of the differences exceeds the threshold, the value of primary interest is accepted. If both of the differences exceed the threshold, the value of primary interest is rejected, and replaced by an interpolated value.

Figure 11:
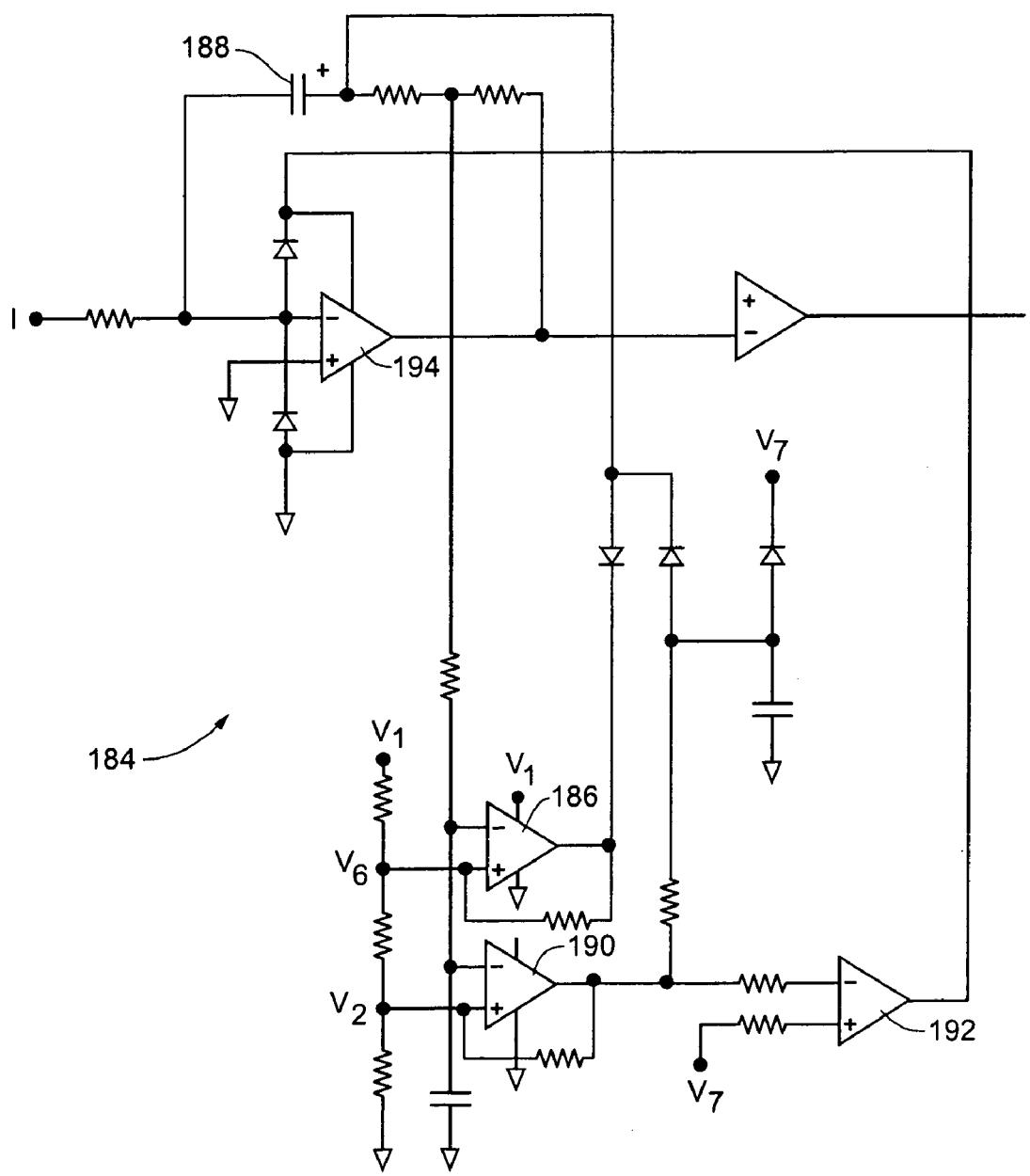

FIG. 11 illustrates an electrometer circuit 184, similar to circuit 84 except that circuit 184 is configured to receive a negative current from its associated electrode, in a system where the center electrode configuration is biased to a negative voltage while the collector electrodes are maintained at ground. Accordingly, the integrator output voltage increases during normal integration. When the condition-monitoring voltage rises above the upper threshold voltage level, a comparator amplifier 186 is switched from a high voltage output to a low voltage output, thus to initiate a rapid discharge of an integrating capacitor 188. The discharge rapidly drives down the integrator output, and also reduces the condition-monitoring voltage, subject to an RC delay as in circuit 84. When the condition-monitoring voltage falls below the upper threshold voltage, discharge is terminated. Due to the delay, the condition-monitoring voltage continues to fall.

When the condition-monitoring voltage falls below the lower threshold voltage level, a comparator amplifier 190 switches its output from the low voltage to the high voltage, initiating charging of the integrating capacitor and acting through an amplifier 192 to cut off power to an operational amplifier 194. When the charging of the capacitor drives the condition-monitoring voltage above the lower threshold voltage, capacitor charging is terminated, power to op amp 194 is restored, and integration of the incoming current resumes.

Figure 12:
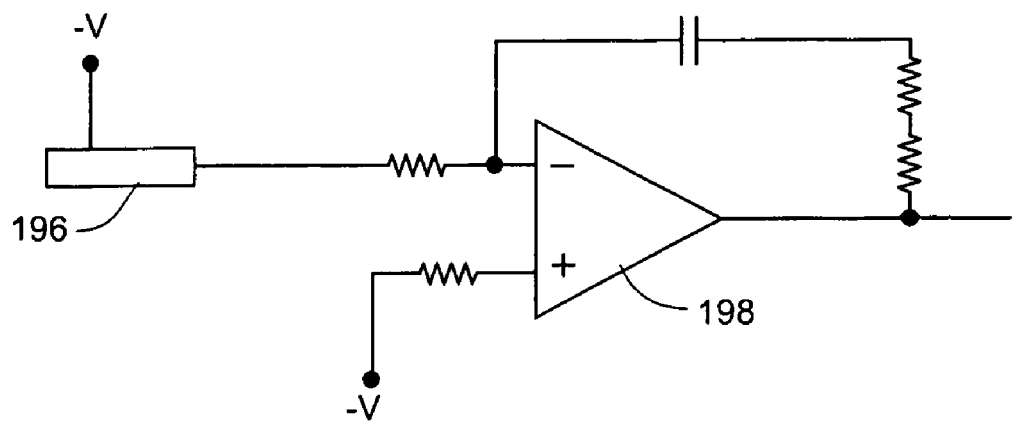

FIG. 12 illustrates part of an instrument similar to spectrometer 16, but in which the center electrode configuration is maintained at ground, and the collector electrodes are negatively biased, increasingly in the downstream direction if desired, to attract positively charged particles. A collector electrode 196 provides incoming current to the negative input terminal of an operational amplifier 198 of an integrating circuit. The positive input terminal of amplifier 198 is biased to a negative voltage V, to match the level at which the associated collector electrode 196 is biased. In other respects, the electrometer circuit is similar to circuit 84, although there is an additional need to interface the integrator output to the digital processing circuitry.

Figure 13:
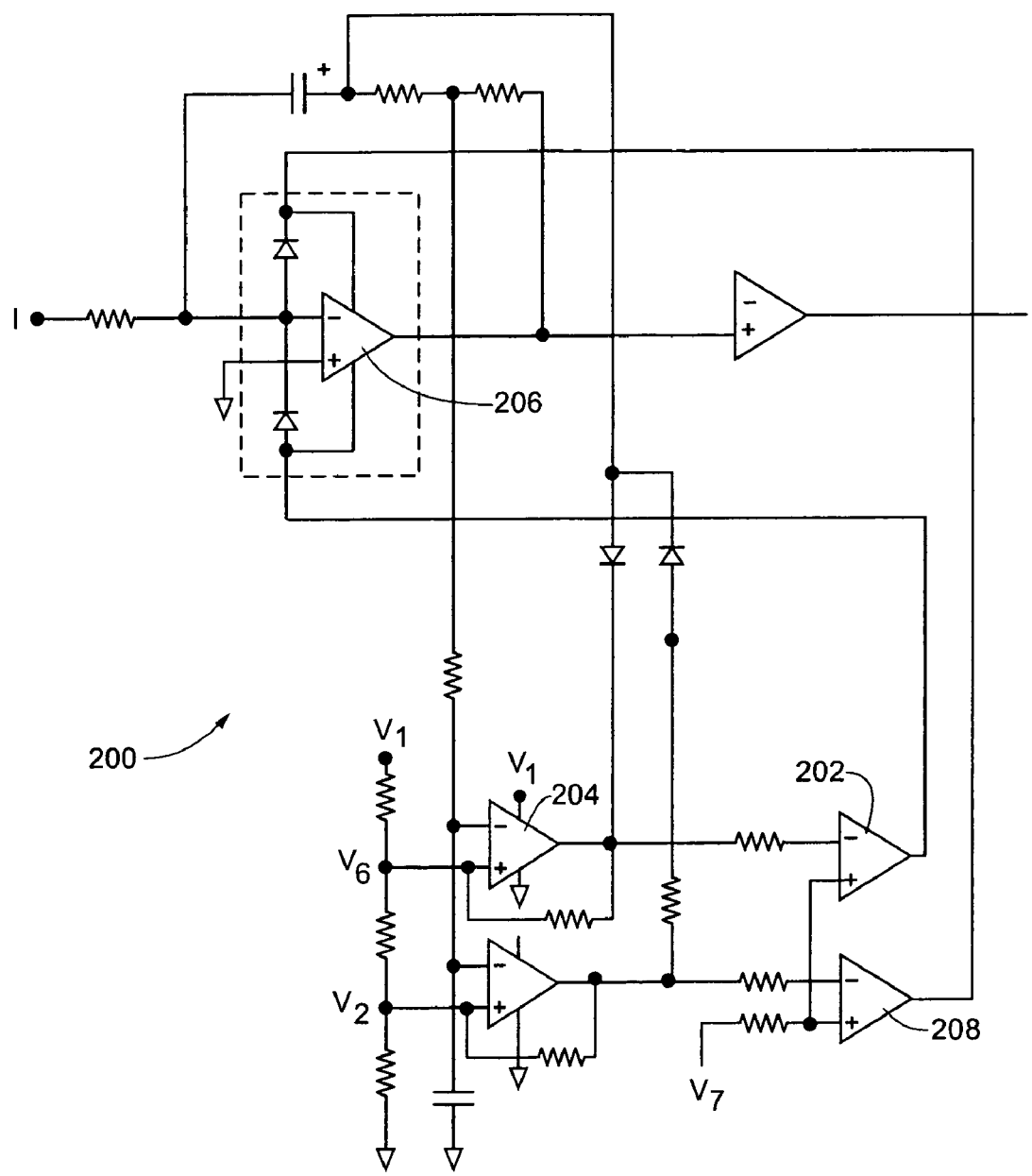

FIG. 13 illustrates a portion of an electrometer circuit 200 similar to circuit 84, except that the circuit is configured to provide a dual polarity response. In circuit 200, a second power control amplifier 202 is coupled to receive the output of a comparator amplifier 204 associated with the high threshold voltage. As the output of comparator amplifier 204 switches from the low voltage to the high voltage, it causes amplifier 202 to switch its output from the low voltage to the high voltage. The output of amplifier 202 is provided as a power input to an operational amplifier 206, opposite to the input from a power control amplifier 208. Amplifier 202 replaces the charge limiting circuitry in circuit 84.

Figure 14:
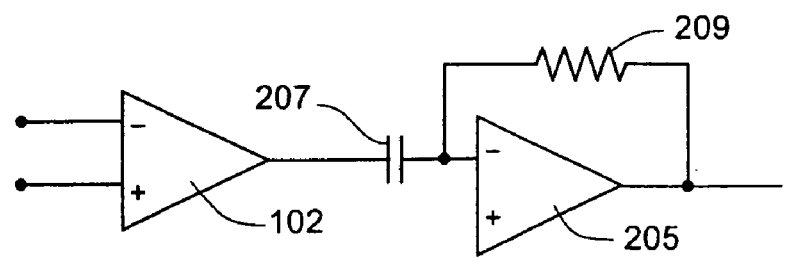

FIG. 14 illustrates part of a circuit substantially identical to integrating electrometer circuit 84, except for the addition of an operational amplifier circuit to differentiate the output of buffer amplifier 102. The output of the buffer amplifier is provided to the negative terminal of an operational amplifier 205, through a capacitor 207. The circuit includes an amplifier feedback loop incorporating a resistor 209.

The output voltage of amplifier 205 reflects the rate of change of the input. Accordingly, the modified circuit provides a stand-alone electrometer with an output that rises and falls to track the incoming current. There is no need to digitally differentiate the analog output. This circuit, like circuit 84, should be augmented with components for selectively ignoring data associated with resetting the integrating capacitor.

FIG. 15 schematically illustrates an alternative particle characterizing instrument 210 including a central electrode 212, and a single collector 214. Central electrode 212 is biased to a high positive voltage to repel positively charged particles, while collector electrode 214 is maintained at ground. To produce a spectrum with instrument 210, the biasing voltage to electrode 212 is stepped through a series of different levels, each level associated with a different range of electrical mobility.

Thus in accordance with the present invention, engine exhausts and other aerosols subject to rapid and extreme fluctuations can be characterized with improved accuracy, and over a broader range of particle sizes. With multiple collector electrodes simultaneously generating electrical currents, a high frequency sampling of data, and integrating circuitry incorporating rapid capacitor charge and discharge functions, a particle spectrometer is capable of generating detailed, accurate and virtually real time particle distribution information. Further, the integrating electrometer with rapid reset cycles is well suited for a wide variety of current measuring applications.

What is claimed is:

1. A reset circuit for an integrating amplifier, including:
   first comparator circuitry having a first input terminal, a second input terminal and a first output terminal;
   a first conductive path adapted to couple the first input terminal to a feedback loop of an integrating amplifier between an integrator output of the integrating amplifier and an integrating capacitor along the feedback loop, whereby a comparator input voltage at the first input terminal is changed in a predetermined first direction and in proportion to an amplitude of an incoming current during integration of the incoming current;
   a substantially stable first voltage source for biasing the second input terminal at a first threshold voltage level selected to determine one end of an operating range for integration, wherein the comparator input voltage, when in said range and when so changed during integration, approaches the first threshold voltage level;
   a second conductive path coupling the first output terminal to the feedback loop;
   power control circuitry having a fifth input terminal coupled to the first output terminal, a third output terminal, and a fourth conductive path adapted to couple the third output terminal to an input of the integrating amplifier to provide power to the integrating amplifier, wherein the power control circuitry is adapted to generate a substantially stable high voltage during integration, and to switch from the high voltage to a substantially stable low voltage in response to receiving the high voltage from the first comparator circuitry, thereby to shut off power to the integrating amplifier;
   wherein the first comparator circuitry is adapted, in response to detecting movement of the comparator input voltage out of the operating range beyond the first threshold voltage level, to generate a predetermined first comparator output voltage level at the first output terminal and to apply the first comparator output voltage level to the feedback loop via the second conductive path, thereby to drive the comparator input voltage in a second direction opposite said first direction to a point within the operating range for further integration of the incoming current;
   wherein the first comparator circuitry further is adapted to stop the application of the first comparator output voltage level to the feedback loop, responsive to detecting movement of the comparator input voltage, during said application, in the second direction beyond the first threshold voltage level and into the operating range;
   wherein the comparator input voltage, when in the operating range, is higher than the first threshold voltage level, and is reduced during integration of the incoming current;
   wherein the substantially stable first comparator output voltage level is a high voltage selected to rapidly charge the integrating capacitor; and
   wherein the first comparator circuitry is adapted to alternatively generate said high voltage and a substantially stable low voltage, wherein applying the first comparator output voltage to the feedback loop consists essentially of switching from the low voltage to the high voltage, and stopping the application to the feedback loop consists essentially of switching from the high voltage to the low voltage.

2. A reset circuit for an integrating amplifier, including:

first comparator circuitry having a first input terminal, a second input terminal and a first output terminal;

a first conductive path adapted to couple the first input terminal to a feedback loop of an integrating amplifier between an integrator output of the integrating amplifier and an integrating capacitor along the feedback loop, whereby a comparator input voltage at the first input terminal is changed in a predetermined first direction and in proportion to an amplitude of an incoming current during integration of the incoming current;

a substantially stable first voltage source for biasing the second input terminal at a first threshold voltage level selected to determine one end of an operating range for integration, wherein the comparator input voltage, when in said range and when so changed during integration, approaches the first threshold voltage level; and a second conductive path coupling the first output terminal to the feedback loop;

limiting circuitry coupled to the second conductive path to prevent excess charging of the integrating capacitor;

wherein the first comparator circuitry is adapted, in response to detecting movement of the comparator input voltage out of the operating range beyond the first threshold voltage level, to generate a predetermined first comparator output voltage level at the first output terminal and to apply the first comparator output voltage level to the feedback loop via the second conductive path, thereby to drive the comparator input voltage in a second direction opposite said first direction to a point within the operating range for further integration of the incoming current;

wherein the first comparator circuitry further is adapted to stop the application of the first comparator output voltage level to the feedback loop, responsive to detecting movement of the comparator input voltage, during said application, in the second direction beyond the first threshold voltage level and into the operating range;

wherein the comparator input voltage, when in the operating range, is higher than the first threshold voltage level, and is reduced during integration of the incoming current; and wherein the substantially stable first comparator output voltage level is a high voltage selected to rapidly charge the integrating capacitor.

3. The circuit of claim 2 wherein the limiting circuit includes a limiting capacitor coupled to be charged simultaneously with charging of the integrating capacitor, and a diode biased to a substantially stable limiting voltage level.

4. A reset circuit for an integrating amplifier, including:

first comparator circuitry having a first input terminal, a second input terminal and a first output terminal;

a first conductive path adapted to couple the first input terminal to a feedback loop of an integrating amplifier between an integrator output of the integrating amplifier and an integrating capacitor along the feedback loop, whereby a comparator input voltage at the first input terminal is changed in a predetermined first direction and in proportion to an amplitude of an incoming current during integration of the incoming current;

a substantially stable first voltage source for biasing the second input terminal at a first threshold voltage level selected to determine one end of an operating range for integration, wherein the comparator input voltage, when in said range and when so changed during integration, approaches the first threshold voltage level;

a second conductive path coupling the first output terminal to the feedback loop:

second comparator circuitry having a third input terminal, a fourth input terminal and a second output terminal, wherein the third input terminal is coupled to receive the comparator input voltage;

wherein the first comparator circuitry is adapted, in response to detecting movement of the comparator input voltage out of the operating range beyond the first threshold voltage level, to generate a predetermined first comparator output voltage level at the first output terminal and to apply the first comparator output voltage level to the feedback loop via the second conductive path, thereby to drive the comparator input voltage in a second direction opposite said first direction to a point within the operating range for further integration of the incoming current;

a substantially stable second voltage source for biasing the fourth input terminal at a second threshold voltage level selected to determine a second and opposite end of the operating range, wherein the comparator input voltage, when in the operating range and when driven in said opposite direction, moves toward the second threshold voltage level;

a third conductive path adapted to couple the second output terminal to the feedback loop;

wherein the second comparator circuitry is adapted, in response to detecting movement of the comparator input voltage in the second direction out of the operating range beyond the second threshold voltage level, to generate a predetermined second comparator output voltage level at the second output terminal and to apply the second comparator output voltage level to the feedback loop via the third conductive path, thereby to drive the comparator input voltage in the first direction to a point within the operating range for further integration of the incoming current;

wherein the comparator input voltage, when in the operating range, is higher than the first threshold voltage level, and lower than the second threshold voltage level, and is reduced during integration of the incoming current;

wherein the first comparator circuitry is adapted to alternatively generate a substantially stable high voltage and a substantially stable low voltage at the first output terminal, and generating the first comparator output voltage level consists essentially of switching from the low voltage to the high voltage to rapidly charge the integrating capacitor;

wherein the first comparator circuitry further is adapted to stop the application of the first comparator output voltage level to the feedback loop, responsive to detecting movement of the comparator input voltage, during said application, in the second direction beyond the first threshold voltage level and into the operating range; and wherein the second comparator circuitry is adapted to alternatively generate a substantially stable high voltage and a substantially stable low voltage at the second output terminal, and generating the second comparator output level consists essentially of switching from the high voltage to the low voltage to rapidly discharge the integrating capacitor.

5. The circuit of claim 4 further including:

power control circuitry having a fifth input terminal coupled to the first output terminal, a third output terminal, and a fourth conductive path adapted to couple the third output terminal to an input of the integrating amplifier to provide power to the integrating amplifier;

wherein the power control circuitry is adapted to generate a substantially stable high voltage during integration, and to switch from the high voltage to a substantially stable low voltage in response to receiving the high voltage from the first comparator circuitry, thereby to shut off power to the integrating amplifier.

6. The circuit of claim 5 wherein:

the power control circuit comprises an operational amplifier with a positive input terminal biased at a substantially stable voltage and a negative input terminal coupled to the first output terminal, and each of the first and second comparator circuitry comprises an operational amplifier with resistive feedback receiving the first comparator input voltage at a negative input terminal.

\* \* \* \* \*

UNITED STATES PATENT AND TRADEMARK OFFICE
CERTIFICATE OF CORRECTION

PATENT NO. : 7,230,431 B2  Page 1 of 1
APPLICATION NO. : 10/765740
DATED : June 12, 2007
INVENTOR(S) : Aadu Mirme It is certified that error appears in the above-identified patent and that said Letters Patent is hereby corrected as shown below:

Column 8, Line 46:
After "output" delete ",".

Column 12, Lines 19 & 24:
Delete "multiply" and insert --multiple--.

Signed and Sealed this

Third Day of June, 2008

JON W. DUDAS
*Director of the United States Patent and Trademark Office*